United States Patent
Kadkly et al.

(10) Patent No.: US 7,746,459 B2
(45) Date of Patent: Jun. 29, 2010

(54) SYSTEMS CONFIGURED TO INSPECT A WAFER

(75) Inventors: Azmi Kadkly, Cupertino, CA (US); Stephen Biellak, Sunnyvale, CA (US); Mehdi Vaez-Iravani, Los Gatos, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 74 days.

(21) Appl. No.: 11/837,220

(22) Filed: Aug. 10, 2007

(65) Prior Publication Data

US 2009/0040525 A1 Feb. 12, 2009

(51) Int. Cl.
    *G01N 21/00* (2006.01)
(52) U.S. Cl. .................. 356/237.2; 356/237.4
(58) Field of Classification Search .... 356/237.1–237.5
     See application file for complete search history.

(56) References Cited

U.S. PATENT DOCUMENTS

| | | | |
|---|---|---|---|
| 5,274,434 A * | 12/1993 | Morioka et al. ......... | 356/237.4 |
| 5,798,829 A | 8/1998 | Vaez-Iravani et al. | |
| 5,805,278 A | 9/1998 | Danko | |
| 6,201,601 B1 | 3/2001 | Vaez-Iravani et al. | |
| 6,256,093 B1 | 7/2001 | Ravid et al. | |
| 6,271,916 B1 | 8/2001 | Marxer et al. | |
| 6,384,910 B2 | 5/2002 | Vaez-Iravani et al. | |
| 6,538,730 B2 | 3/2003 | Vaez-Iravani et al. | |
| 6,590,645 B1 | 7/2003 | Chen et al. | |
| 6,606,153 B2 | 8/2003 | Marxer et al. | |
| 6,618,134 B2 | 9/2003 | Vaez-Iravani et al. | |
| 6,639,662 B2 | 10/2003 | Vaez-Iravani et al. | |
| 6,657,715 B2 | 12/2003 | Vaez-Iravani et al. | |
| 6,791,680 B1 * | 9/2004 | Rosengaus et al. ....... | 356/237.2 |
| 6,862,096 B2 | 3/2005 | Vaez-Iravani et al. | |
| 6,879,390 B1 | 4/2005 | Kvamme et al. | |
| 6,891,611 B1 | 5/2005 | Vaez-Iravani et al. | |
| 6,956,644 B2 | 10/2005 | Biellak et al. | |
| 6,999,183 B2 | 2/2006 | Nielson et al. | |
| 7,002,677 B2 | 2/2006 | Bevis et al. | |
| 7,016,031 B2 | 3/2006 | Chen et al. | |
| 7,038,772 B2 | 5/2006 | Chen et al. | |
| 7,038,773 B2 | 5/2006 | Kuhlmann et al. | |
| 7,061,598 B1 | 6/2006 | Bevis et al. | |

(Continued)

OTHER PUBLICATIONS

U.S. Appl. No. 11/110,383, filed Apr. 20, 2005, Shortt et al.

(Continued)

*Primary Examiner*—Michael P Stafira
(74) *Attorney, Agent, or Firm*—Ann Marie Mewherter

(57) ABSTRACT

Systems configured to inspect a wafer are provided. One system includes an illumination subsystem configured to illuminate an area on the wafer by directing light to the wafer at an oblique angle of incidence. The system also includes a collection subsystem configured to simultaneously collect light scattered from different spots within the illuminated area and to focus the light collected from the different spots to corresponding positions in an image plane. In addition, the system includes a detection subsystem configured to separately detect the light focused to the corresponding positions in the image plane and to separately generate output responsive to the light focused to the corresponding positions in the image plane. The output can be used to detect defects on the wafer.

29 Claims, 3 Drawing Sheets

U.S. PATENT DOCUMENTS

| | | |
|---|---|---|
| 7,064,821 B2 | 6/2006 | Vaez-Iravani et al. |
| 7,068,363 B2 | 6/2006 | Bevis et al. |
| 7,079,238 B2 | 7/2006 | Vaez-Iravani et al. |
| 7,102,744 B2 | 9/2006 | Marxer et al. |
| 7,106,432 B1 | 9/2006 | Mapoles et al. |
| 7,116,413 B2 | 10/2006 | Vaez-Iravani et al. |
| 7,119,897 B2 | 10/2006 | Vaez-Iravani et al. |
| 7,130,036 B1 | 10/2006 | Kuhlmann et al. |
| 7,130,039 B2 * | 10/2006 | Vaez-Iravani et al. .... 356/237.5 |
| 7,184,138 B1 | 2/2007 | Li |
| 7,199,874 B2 | 4/2007 | Bevis et al. |
| 7,206,066 B2 | 4/2007 | Vurens et al. |
| 7,218,392 B2 | 5/2007 | Biellak et al. |
| 7,218,768 B2 | 5/2007 | Evans et al. |
| 7,271,921 B2 | 9/2007 | Shortt |
| 7,304,310 B1 | 12/2007 | Shortt et al. |
| 7,463,349 B1 * | 12/2008 | Biellak et al. ............ 356/237.2 |
| 2004/0057045 A1 | 3/2004 | Vaez-Iravani et al. |
| 2005/0018181 A1 | 1/2005 | Vaez-Iravani et al. |
| 2005/0206886 A1 | 9/2005 | Vaez-Iravani et al. |
| 2006/0092427 A1 | 5/2006 | Nielsen et al. |
| 2006/0109457 A1 | 5/2006 | Miller et al. |
| 2006/0274304 A1 | 12/2006 | Haller et al. |
| 2006/0285112 A1 | 12/2006 | Reich et al. |
| 2007/0076208 A1 * | 4/2007 | Koo .......................... 356/451 |
| 2007/0081151 A1 | 4/2007 | Shortt et al. |
| 2007/0103676 A1 | 5/2007 | Marxer et al. |
| 2007/0132987 A1 | 6/2007 | Haller et al. |
| 2007/0229809 A1 | 10/2007 | Belyaev et al. |

OTHER PUBLICATIONS

U.S. Appl. No. 11/228,584, filed Sep. 16, 2005, Zhao et al.
U.S. Appl. No. 11/673,150, filed Feb. 9, 2007, Kirk et al.
U.S. Appl. No. 11/745,127, filed May 7, 2007, Shortt et al.
U.S. Appl. No. 11/751,970, filed May 22, 2007, Chen et al.
International Search Report and Written Opinion for PCT/US08/009571 mailed Feb. 27, 2009.

* cited by examiner

SYSTEMS CONFIGURED TO INSPECT A WAFER

BACKGROUND OF THE INVENTION

1. Field of the Invention

This invention generally relates to systems configured to inspect a wafer. Certain, embodiments relate to a system configured to illuminate an area on the wafer and to detect light scattered from different spots within the illuminated area.

2. Description of the Related Art

The following description and examples are not admitted to be prior art by virtue of their inclusion in this section.

Fabricating semiconductor devices such as logic and memory devices typically includes processing a substrate such as a semiconductor wafer using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a single semiconductor wafer and then separated into individual semiconductor devices.

Inspection processes are used at various steps during a semiconductor manufacturing process to detect defects on wafers to promote higher yield in the manufacturing process and thus higher profits. Inspection has always been an important part of fabricating semiconductor devices such as integrated circuits. However, as the dimensions of semiconductor devices decrease, inspection becomes even more important to the successful manufacture of acceptable semiconductor devices because smaller defects can cause the device to fail. For instance, as the dimensions of semiconductor devices decrease, detection of defects of decreasing size has become necessary since even relatively small defects may cause unwanted aberrations in the semi conductor devices. Accordingly, much work has been done in the field of wafer inspection to increase the sensitivity of inspection systems to smaller and smaller defects.

Another concern that becomes more prevalent for inspection system manufacturers and customers alike as defect sizes decrease is the difficulty of detecting relatively small defects on relatively rough wafer surfaces. In particular, previously, the scattering of light from relatively rough surfaces did not substantially limit inspection system performance since the defects being detected were relatively large. However, as the size of defects decreases, the amount of light scattered from the defects may also decrease. As such, the amount of light scattered from defects of relatively small size may be much closer to the amount of light scattered from relatively rough surfaces thereby reducing the sensitivity of many systems for inspection of such surfaces. Therefore, although many currently available inspection systems are capable of detecting relatively large defects on relatively rough surfaces and/or relatively small defects on relatively smooth surfaces, there is still a need for an inspection system that can detect relatively small defects on relatively rough surfaces.

Many inspection systems such as those described above are configured to image a single spot or line on the wafer at normal and/or oblique angles of incidence using spherical and/or cylindrical lenses. The single spot or line imaging of these systems also contributes, at least in part, to the relatively low sensitivity (e.g., relatively low signal-to-noise ratio, SNR) of the systems for inspection of rough surfaces. In particular, since a single spot or line on the wafer plane is relatively large (particularly in comparison to the size of the defects typically being detected), the light scattered from the illuminated spot or line will contain a relatively large amount of scattering from the surface of the wafer. Such scattering may be relatively low for relatively smooth surfaces. However, the scattered light from relatively rough wafer surfaces may be much higher and will, therefore, adversely affect the sensitivity of the inspection system.

Obviously, therefore, one way to increase the SNR for relatively rough surface inspection is to decrease die size of the spot on the wafer. However, decreasing the size of the optical spot on the wafer will decrease the throughput of the inspection system, and single spot scanning-based systems already have relatively slow scanning rates. As such, attempts have been made to image multiple smaller spots on a wafer such that a larger area of the wafer can be illuminated simultaneously by the multiple spots thereby maintaining the throughput of the inspection system without causing relatively large amounts of scattering from the surface of the wafer.

Accordingly, it would be advantageous to develop systems and methods for providing relatively high sensitivity inspection capability of wafers, particularly in terms of absolute defect sensitivity and sensitivity for relatively rough surface inspection, while meeting, or even exceeding, throughput requirements.

SUMMARY OF THE INVENTION

The following description of various system embodiments is not to be construed in any way as limiting the subject matter of the appended claims.

One embodiment relates to a system configured to inspect a wafer. The system includes an illumination subsystem configured to illuminate an area on the wafer by directing light to the wafer at an oblique angle of incidence. The system also includes a collection subsystem configured to simultaneously collect light scattered from different spots within the illuminated area and to focus the light collected from the different spots to corresponding positions in an image plane. In addition, the system includes a detection subsystem configured to separately detect the light focused to the corresponding positions in the image plane and to separately generate output responsive to the light focused to the corresponding positions in the image plane. The output can be used to detect defects on the wafer.

In one embodiment, the different spots within the illuminated area do not overlap with each other within the illuminated area. In another embodiment, a size of each of the different spots on the wafer is approximately equal.

In one embodiment, a size of each of the different spots on the wafer is selected such that a substantial amount of the light scattered from the different spots is not scattered from a surface of the wafer. In another embodiment, each of the different spots is configured such that an amount of haze collected from each of the different spots is significantly less than an amount of haze associated with the illuminated area on the wafer. In an additional embodiment, each of the different spots is configured such that a direct current (DC) light level due to haze collected from each of the different spots is significantly less than a DC light level due to haze associated with the illuminated area on the wafer. In a further embodiment, each of the different spots is configured such that spatial noise collected from each of the different spots due to roughness of the wafer is significantly less than spatial noise associated with the illuminated area on the wafer due to the roughness of the wafer.

In one embodiment, the collection subsystem includes an optical element configured to simultaneously collect the light scattered from the different spots. In one such embodiment, a section of the optical element is removed such that the illumination subsystem can direct the light through the section to the area on the wafer at the oblique angle of incidence.

In some embodiments, the wafer includes an unpatterned wafer. In other embodiments, the wafer includes a patterned wafer. In one such embodiment, the system is configured to scan the light directed to the patterned wafer across the patterned wafer in x and y directions.

In one embodiment, the collection subsystem includes a miniaturized refractive optical element configured to simultaneously collect the light scattered from the different spots. In another embodiment, the collection subsystem includes a refractive optical element configured to simultaneously collect the light scattered from the different spots, and the refractive optical element has a size allowing the system to move the refractive optical element during scanning of the light over the wafer in response to changes in focus of the collection subsystem. In an additional embodiment, the collection subsystem is corrected such that the light scattered from the different spots is imaged to the corresponding positions in the image plane with a defined point spread function (PSF).

In some embodiments, the system is configured to scan the light directed to the wafer across the wafer by simultaneously rotating and translating the wafer.

In one embodiment, the detection subsystem includes a detector array configured to separately detect the light focused to the corresponding positions in the image plane. In another embodiment, the detection subsystem includes a set of optical fibers configured to separately transmit the light from the corresponding positions in the image plane to different detectors of the detection subsystem. Each of the embodiments of the system described above may be further configured as described herein.

Another embodiment relates to a system configured to inspect a patterned wafer. The system includes an illumination subsystem configured to simultaneously illuminate multiple spots on the patterned wafer at a substantially normal angle of incidence. The system also includes a collection subsystem configured to separately collect light from the multiple spots and to focus the light collected from the multiple spots to corresponding positions in an image plane. In addition, the system includes a detection subsystem configured to separately detect the light focused to the corresponding positions in the image plane and to separately generate output responsive to the light focused to the corresponding positions in the image plane. The output can be used to detect defects on the patterned wafer.

In one embodiment, the multiple spots do not overlap with each other on the patterned wafer. In another embodiment, the light from the multiple spots includes scattered light. In an additional embodiment, the light from the multiple spots includes reflected light.

In one embodiment, a size of each of the multiple spots on the patterned wafer is approximately equal. In another embodiment, a size of each of the multiple spots on the patterned wafer is selected such that a substantial amount of the light collected from the multiple spots is not scattered from a surface of the patterned wafer.

In one embodiment, each of the multiple spots is configured such that an amount of haze collected from each of the multiple spots is significantly less than an amount of haze associated with an area covered by all of the multiple spots on the patterned wafer. In another embodiment, each of the multiple spots is configured such that a DC light level due to haze collected from each of the multiple spots is significantly less than a DC light level associated with an area covered by all of the multiple spots on the patterned wafer. In an additional embodiment, each of the multiple spots is configured such that spatial noise collected from each of the multiple spots due to roughness of the patterned wafer is significantly less than spatial noise associated with an area covered by all of the multiple spots on the patterned wafer due to the roughness of the patterned wafer.

In one embodiment, the collection subsystem includes a miniaturized refractive optical element configured to collect the light from the multiple spots. In another embodiment, the collection subsystem includes a refractive optical element configured to collect the light from the multiple spots, and the refractive optical element has a size allowing the system to move the refractive optical element during scanning of the patterned wafer in response to changes in focus of the collection subsystem. In an additional embodiment, the collection subsystem is corrected such that the light from the multiple spots is imaged to the corresponding positions in the image plane with a defined PSF.

In one embodiment, the system is configured to scan light directed to the multiple spots on the patterned wafer across the patterned wafer by simultaneously rotating and translating the patterned water.

In some embodiments, the detection subsystem includes a detector array configured to separately detect the light focused to the corresponding positions in the image plane. In another embodiment, the detection subsystem includes a set of optical fibers configured to separately transmit the light from the corresponding positions in the image plane to different detectors of the detection subsystem. Each of the embodiments of the system described above may be further configured as described herein.

BRIEF DESCRIPTION OF THE DRAWINGS

Other objects and advantages of the invention will become apparent upon reading the following detailed description and upon reference to the accompanying drawings in which.

Figure 1:
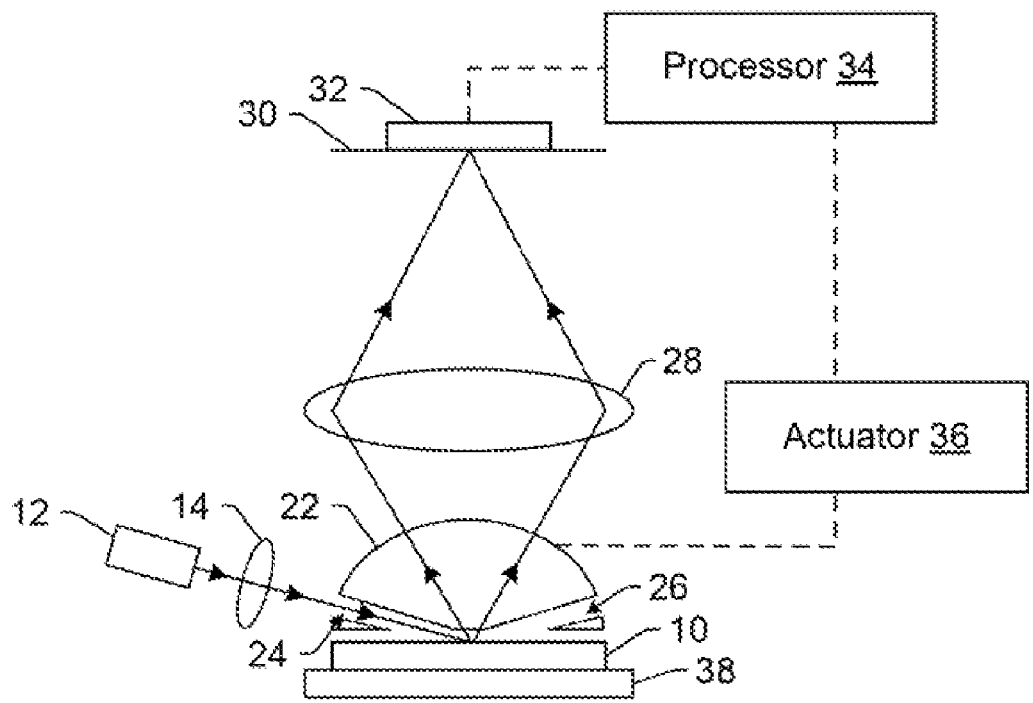
FIG. 1 is a schematic diagram illustrating a cross-sectional view of one embodiment of a system configured to inspect a wafer.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

One or more layers may be formed upon a wafer. For example, such layers may include, but are not limited to, a resist, a dielectric material, a conductive material, and a semiconductive material. Many different types of such layers are known in the art, and the term wafer as used herein is intended to encompass a wafer on which all types of such layers may be formed.

One or more layers formed on a wafer may be patterned or unpatterned. For example, a wafer may include a plurality of dies, each having repeatable patterned features. Formation and processing of such layers of material may ultimately result in completed devices. Many different types of devices may be formed on a wafer, and the terra wafer as used herein is intended to encompass a wafer on which any type of device known in the art is being fabricated.

Although embodiments are described herein with respect to wafers, it is to be understood that the embodiments may be used for inspection of another specimen such as a reticle, which may also be commonly referred to as a mask or a photomask. Many different types of reticles are known in the art, and the terms "reticle," "mask," and "photomask" as used herein are intended to encompass all types of reticles known in the art.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

FIG. 1 illustrates one embodiment of a system configured to inspect a wafer. The system includes an illumination subsystem configured to illuminate an area on wafer 10 by directing light to the wafer at an oblique angle of incidence. For example, as shown in FIG. 1, the illumination subsystem includes light source 12. Light source 12 may include any suitable light source such as a laser, a cw laser, or a pulsed laser. In addition, light source 12 may be configured to generate light at any suitable wavelength(s) (e.g., about 355 nm or about 266 nm). Light source 12 is configured to direct the light to refractive optical element 14. Refractive optical element 14 may be configured to focus the light from light source 12 to wafer 10 at an oblique angle of incidence as shown in FIG. 1. Refractive optical element 14 may include any suitable refractive optical element known in the art. In addition, refractive optical element 14 may be replaced with one or more refractive optical elements and/or one or more reflective optical elements. The illumination subsystem may be configured to direct the light to the wafer at any suitable oblique angle of incidence.

Figure 2:
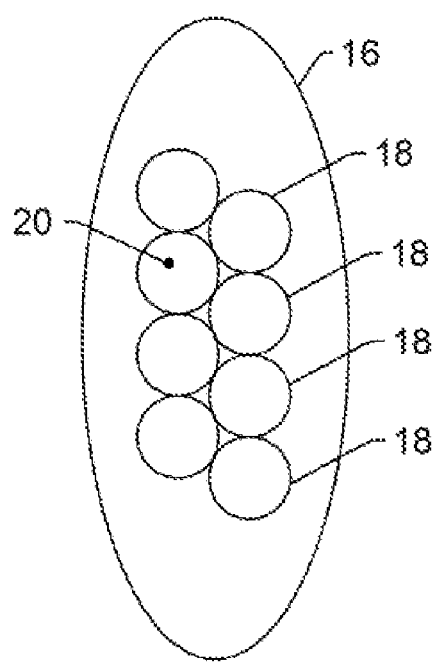
FIG. 2 is a schematic diagram illustrating a plan view of one embodiment of an illuminated area on a wafer and different spots within the illuminated area from which light is collected.

The system shown in FIG. 1 also includes a collection subsystem configured to simultaneously collect light scattered from different spots within the illuminated area and to focus the light collected from the different spots to corresponding positions in an image plane. The different spots within the illuminated area may be configured as shown in FIG. 2. For example, as shown in FIG. 2, an illumination subsystem such as that described above may be configured to illuminate area 16 on a wafer (not shown in FIG. 2) as described herein. In addition, as shown in FIG. 2, a collection subsystem such as that described further herein may be configured to simultaneously collect light scattered from different spots 18 within illuminated area 16 as described herein and to focus the light collected from different spots 18 to corresponding positions in an image plane as described further herein. In this manner, the positions of the different spots within the illuminated area shown in FIG. 2 correspond to the image of the corresponding positions in an image plane as described herein (e.g., to the image of the optical fiber collectors on the wafer surface). As such, the system embodiments described herein may be configured for oblique illumination combined with a multi-head collector, which may be configured as described further herein. In one embodiment as shown in FIG. 2, different spots 18 within illuminated area 16 do not overlap with each other in the illuminated area. In addition, although the different spots are shown in FIG. 2 as positioned adjacent to each other within the illuminated area on the wafer, the different spots may be spatially separated from each other within the illuminated area on the wafer. In another embodiment as shown in FIG. 2, a size of each of different spots 18 on the wafer is approximately equal.

In one embodiment, a size of each of the different spots on the wafer is selected such that a substantial amount of the light scattered from the different spots is not scattered from a surface of the wafer. For example, as shown in FIG. 2, a ratio of the area of different spots 18 to the area of defect 20 is substantially smaller than a ratio of the area of illuminated area 16 to the area of defect 20. Therefore, the ratio of the light scattered from the defect to the light scattered from the different spot in which the defect is located will advantageously be substantially larger than the ratio of the light scattered from the defect to the light scattered from the illuminated area. As such, in some instances, it may be advantageous to configure the collection subsystem such that the size of the different spots on the wafer is just slightly larger than the size of the defects that are to be detected on the wafer. In this manner, the amount of scattered light collected from the different spots on the wafer that is not light scattered from a defect within the different spots may be minimized thereby maximizing noise reduction and maximizing defect sensitivity. As such, the embodiments described herein provide a sensitivity enhancement in the detection of relatively small defects.

In another embodiment, each of the different spots is configured such that an amount of haze collected from each of the different spots is significantly less than an amount of haze associated with the illuminated area on the wafer. For example, each of the different spots may be configured such that the haze associated with the wafer surface scattering is collected over a relatively small region of the illuminated area. For example, if the magnification of the system is set such that the collected light per different spot (and therefore per channel) corresponds to a circle having a diameter of about 2 μm, the reduction in the amount of haze collected from the different spots compared with the amount of haze collected from the 10 μm×60 μm, high sensitivity, spot of the SP2 system, which is commercially available from KLA-Tencor, San Jose, Calif., amounts to a factor of about 150.

In an additional embodiment, each of the different spots is configured such that a direct current (DC) light level, due to haze collected from each of the different spots is significantly less than a DC light level due to haze associated with the illuminated area on the wafer. For example, as described above, each of the different spots may be configured such that an amount of haze collected from each of the different spots is significantly less than an amount of haze associated with the illuminated area on the wafer. Such a configuration of the different spots has an additional advantage in that such a configuration reduces the DC light level due to wafer haze thereby reducing the shot noise by a factor of more than about 10. For example, the haze signal can be reduced as described above by about 2 orders of magnitude thereby resulting in a factor of about 10 reduction in the shot noise.

In a further embodiment, each of the different spots is configured such that spatial noise collected from each of the different spots due to roughness of the wafer is significantly less than spatial noise associated with the illuminated area on the wafer due to the roughness of the wafer. For example, as described above, each of the different spots may be configured such that an amount of haze collected from each of the different spots is significantly less than an amount of haze associated with the illuminated area on the wafer. Such a configuration of the different spots has an advantage in that such a configuration significantly reduces the spatial noise due to wafer roughness. In certain cases in which the surface roughness is ordinarily rather high such that the maximum sensitivity of currently used inspection systems cannot he achieved, the embodiments described herein may be capable of achieving such levels of sensitivity and performance by virtue of such background noise reductions.

In one embodiment, as shown in FIG. 1, the collection subsystem includes optical element 22 configured to simultaneously collect the light scattered from the different spots. In one such embodiment, section 24 of optical element 22 is removed such that the illumination subsystem can direct the light through the section to the area on the wafer at the oblique angle of incidence. In addition, in such an embodiment, section 26 of optical element 22 may also be removed such that any light reflected from the area on the wafer passes through the opening formed by removing section 26. Optical element 22 may be the first element of an objective lens of the collection subsystem. In this manner, the first element of the collection subsystem (e.g., the first element of the objective lens of the collection subsystem) may have two diagonally opposite holes on the sides of the element thereby forming an illumination channel at an oblique angle of incidence (e.g., about 70 degrees to the surface normal). Optical element 22 may be further configured as described herein.

Light specularly reflected from the wafer that passes through the opening formed by removing section 26 may or may not be detected. For example, such light may be detected and used for defect detection using a collection and detection channel that may be configured as described herein. In this manner, the inspection system may include a bright field (BF) channel. In addition, such light may be detected and used for determining the position of the wafer with respect to the collection subsystem and for auto-focusing of the inspection system. For example, output responsive to the light passing through the opening formed by removing section 26 may be used by a control subsystem described herein to alter a position of one or more optical elements of the system.

The collection subsystem may also include one or more additional optical elements that, in combination with optical element 22, are configured to focus the light collected from the different spots to corresponding positions in an image plane. For example, as shown in FIG. 1, the collection subsystem may include refractive optical element 28 that is configured to focus the light collected by optical element 22 to image plane 30. Therefore, optical element 22 in combination with refractive optical element 28 may form the objective of the collection subsystem. Refractive optical element 28 may include any suitable refractive optical element known in the art. In addition, refractive optical element 28 may be replaced with one or more refractive optical elements and/or one or more reflective optical elements, which may include any suitable refractive and/or reflective optical element(s) known in the art arranged in any suitable configuration known in the art.

For example, such refractive optical element(s) may include, but are not limited to, a tube lens, a relay lens, a collimating lens, a focusing lens, a condenser lens, or some combination thereof.

In one embodiment, the collection subsystem is configured such that the light scattered from the different spots is imaged to the corresponding positions in the image plane with a defined point spread function (PSF). In this manner, the collection subsystem may form a well corrected imaging system. As such, the wafer may be scanned by the system as described further herein, and any relatively small defect, illuminated with p- or s-polarized light, scatters a certain amount of radiation. Since the collection subsystem is well corrected, the scattered radiation is imaged on a particular part of the image plane, with a well defined PSF.

The system shown in FIG. 1 also includes a detection subsystem configured to separately detect the light focused to the corresponding positions in the image plane and to separately generate output responsive to the light focused to the corresponding positions in the image plane. The output can be used to detect defects on the wafer. For example, as shown in FIG. 1, the detection subsystem includes detector 32. Detector 32 is configured to separately detect the light focused to the corresponding positions in the image plane and to separately generate output responsive to the light focused to tire corresponding positions in the image plane. For example, in one embodiment, detector 32 includes a detector array configured to separately detect the light focused to the corresponding positions in the image plane. The detector array may be positioned such that the photosensitive surface of the detector array is substantially planar with the image plane. In this manner, since the collection subsystem is well corrected, the scattered radiation is imaged on a particular part of the detector array, with a well defined PSF. As such, the different positions in the image plane corresponding to the different spots on the wafer may be imaged onto different positions of the detector array. The use of a detector array, rather than a single detector, ensures that haze associated with the wafer surface scattering is detected over a relatively small region of the illuminated area. Each of the different portions of the detector array corresponding to the different positions in the image plane may therefore produce output corresponding to the light focused to only that different position. As such, different output generated by the detector array may correspond to different, spots on the wafer. Each of these different portions may, therefore, form a different detection channel of the inspection system. Therefore, the system shown in FIG. 1 may be essentially a multi-channel inspection system.

The detector array may include any suitable detector array known in the art such as a charge coupled device (CCD) or a time delay integration (TDI) detector. In another example, the detection subsystem may include another detector such as a multi-anode photomultiplier tube (PMT) or any other segmented detector known in the art. In this manner, the single detector preferably generates different output for the light focused to each of the different positions in the image plane. Such detector arrays and segmented detectors may also be used in detection subsystems that include a set of optical fibers as described further herein. In such embodiments, the individual photosensitive areas of the detector may be positioned as described herein with respect to a set of optical fibers. The output generated by the detector or the detector array may include any suitable output such as signals, data, or image data.

The output generated by the detection subsystem may be provided to a processor or computer system. For example, the system may include processor 34 that is coupled to detector 32 (e.g., via one or more transmission media shown by the dashed line between the processor and the detector in FIG. 1, which may include any suitable transmission media known in the art). Processor 34 may be coupled to the detector such that the processor can receive the output generated by the detector. The processor may be configured to use the output generated by the detector to detect defects on the wafer. The processor may be configured to use the output and any suitable algorithm and/or method known in the art to detect defects on the wafer. In addition, processor 34 may be configured to separately process output corresponding to different spots on the wafer. For instance, processor 34 may be configured to determine if output corresponding to different spots on the wafer is responsive to defects on the wafer. For example, the processor may be configured to separately compare the output generated for each of the different spots on the wafer to a threshold. If the output generated for one of the different spots is above the threshold, the processor may determine that a defect is present in the spot thereby detecting a defect in the spot. In contrast, if the output generated for one of the different spots is below the threshold, the processor may determine that a defect is not present in the spot thereby not detecting a defect in the spot. In this manner, the processor may be configured to separately analyze the light scattering from each spot on the wafer. The processor may also be configured to perform other defect-related functions such as defect classification.

A computer system in which the processor is included may take various forms, including a personal computer system, image computer, mainframe computer system, workstation, network appliance, Internet appliance, or other device. In general, the term "computer system" may be broadly defined to encompass any device having one or more processors, which executes instructions from a memory medium. The computer system may also include any suitable processor known in the art such as a parallel processor. In addition, the computer system may include a computer platform with high speed processing and software, either as a standalone or a networked tool.

In one embodiment, the collection subsystem includes a miniaturized refractive optical element configured to simultaneously collect the light scattered from the different spots. For example, optical element 22 described above may be configured as a miniaturized refractive optical element configured to simultaneously collect the light scattered from the different spots. In one such example, optical element 22 may be miniaturized in that it has a mass that is less than a few grams or even less than about 1 g. In another such example, optical element 22 may be miniaturized in that it has a size on the order of about a few cm (e.g., about 1 cm in diameter, about 1 cm by about 1 cm, or between about 5 mm to about 15 mm). Therefore, the optical element may be comparable in size to optics included in a compact disc (CD) or digital video disc (DVD) player. In addition, any other optical elements (e.g., refractive optical element 28) of the collection subsystem maybe miniaturized as well as described above (e.g., miniaturized with respect to mass and size). In this manner, the collection subsystem may include a miniature objective, the first element of which has side holes as described above to accommodate the oblique illumination channel. As such, the systems described herein may be configured to include and use miniaturized optics. In addition, as described above, the system may be configured as a multi-channel inspection system. Therefore, the system may be configured as an enhanced multi-channel inspection system using miniaturized optics.

In another embodiment, the collection subsystem includes a refractive optical element configured to simultaneously collect the light scattered from the different spots, and the refractive optical element has a size allowing the system to move the refractive optical element during scanning of the light over the wafer in response to changes in focus of the collection subsystem. Therefore, the systems described herein provide a new approach to wafer inspection (patterned and unpatterned) in general using miniaturized optics and fast focusing action (e.g., about 1 kHz to about a few kHz or even faster). For example, as described above, the collection subsystem may include a relatively small, fast focusable, objective. In addition, an issue that does arise from high-resolution imaging applications such as those that may be performed by the system embodiments described herein is the auto-focusing requirements. However, since the system embodiments described herein use a miniaturized objective, fast focusing is easily achieved using, for example, piezoelectric actuators. Since the system embodiments described herein are subject to the same considerations as those pertaining to currently used oblique illumination-based inspection systems, the embodiments described herein may use a relatively simple auto-focus subsystem that is used in current inspection system platforms (e.g., the platform of the SPx series of tools commercially available from KLA-Tencor). Therefore, the embodiments described herein may use miniaturized optics in a fast focusing setup in conjunction with single spot illumination and multi-spot collection.

In one such embodiment, the processor described above may be configured to use the output generated by the detection subsystem to determine if the focus of the collection subsystem has changed. The processor may use the output generated by the detection subsystem and any suitable algorithm and/or method to determine if the focus of the collection subsystem has changed or is out of focus. In addition, the system may include a control subsystem coupled to the processor and the refractive optical element(s) of the collection subsystem. The control subsystem may be configured to receive output from the processor regarding the focus of the collection subsystem. In addition, the control subsystem may be configured to use the output to determine how the position(s) of the refractive optical elements) should be altered in response to the focus of the collection subsystem. The control subsystem may also be configured to alter the position(s) of the refractive optical element(s) in response to the focus of the collection subsystem.

In one such embodiment, the system shown in FIG. 1 may include a control subsystem that includes actuator 36. Actuator 36 may be, in one embodiment, a piezoelectric actuator (e.g., or other relatively simple actuators), and the use of such actuators is made possible by the miniaturized optics of the system as described further above. The actuator may be coupled to the processor and refractive optical element 22 as shown by the dashed lines in FIG. 1. The actuator may be coupled to the processor as described above. In addition, the actuator may be coupled to the refractive optical element in any suitable manner such that the actuator can control, the position of the refractive optical element. In this manner, upon receiving output from the processor indicating that the focus of the collection subsystem has changed or is out of focus, the actuator can use this output to determine how the position of the refractive optical element should be altered and to alter the position of the refractive optical element in an appropriate manner. In another embodiment, upon receiving output from the processor indicating how the position of the refractive optical element should be altered, the actuator can use this output to alter the position of the refractive optical element in an appropriate manner. In this embodiment, therefore, the processor may form a part of the control subsystem. In addition, the actuator may be coupled to and configured to alter a position of one or more optical elements of the collection subsystem such that the actuator can alter the focus of the system. For example, the actuator may be coupled to optical element 22 and refractive optical element 28 as described above and may be configured to move both optical elements 22 and 28 as described above.

The system may be configured to scan the light over the wafer in a number of different manners. In addition, the manner in which the system scans the light over the wafer may vary depending on the wafer itself. For example, in one embodiment, the wafer includes an unpatterned wafer. In one such embodiment, the system is configured to scan the light directed to the wafer across the wafer by simultaneously rotating and translating the wafer. In another embodiment, the wafer includes a patterned wafer. In one such embodiment, the system is configured to scan the light directed to the patterned wafer across the patterned wafer in the x and y directions. In either embodiment, the system may be configured to scan the light over the wafer by controlling the position of stage 38 on which the wafer is disposed during inspection. Stage 38 may include any suitable mechanical and/or robotic assembly known in the art.

The system may also Include one or more additional channels (not shown in FIG. 1). In one example, two detection subsystems may be coupled to the collection subsystem. One of the detection subsystems may be configured to detect light collected by the collection subsystem at relatively narrow angles (e.g., angles relatively close to normal), and the other detection subsystem may be configured to detect light collected by the collection subsystem at relatively wide angles (e.g., angles relatively far from normal). For example, the numerical aperture (NA) of the objective of the collection subsystem may be segmented (e.g., using a reflective optical element) such that light collected across a first portion of the NA is directed to a first detection subsystem while light collected across a second portion of the NA is directed to a second detection subsystem.

The one or more additional channels may also or alternatively include a channel configured to collect and detect substantially normal angle of incidence illumination scattered from the wafer at different angles (e.g., different polar and/or azimuthal angles). Substantially normal angle of incidence illumination may be provided by an illumination subsystem configured as described further herein. Therefore, the system shown in FIG. 1 may include one or more illumination channels (e.g., one illumination channel configured to direct light to the wafer at an oblique angle of incidence and one illumination channel configured to direct light to the wafer at a substantially normal angle of incidence).

Furthermore, the one or more additional channels may include a channel configured to collect and detect light reflected from the wafer, and such a channel may be configured as described above. In such embodiments, the illumination may be directed to the wafer at an oblique or substantially normal angle of incidence. Such illumination may be provided by an illumination subsystem described herein, and the illumination subsystem may form one illumination channel of the system. In this manner, the system shown in FIG. 1 may include one or more collection and detection channels and one or more illumination channels. The system shown in FIG. 1 may be further configured according to any other embodiment(s) described herein.

Figure 3:
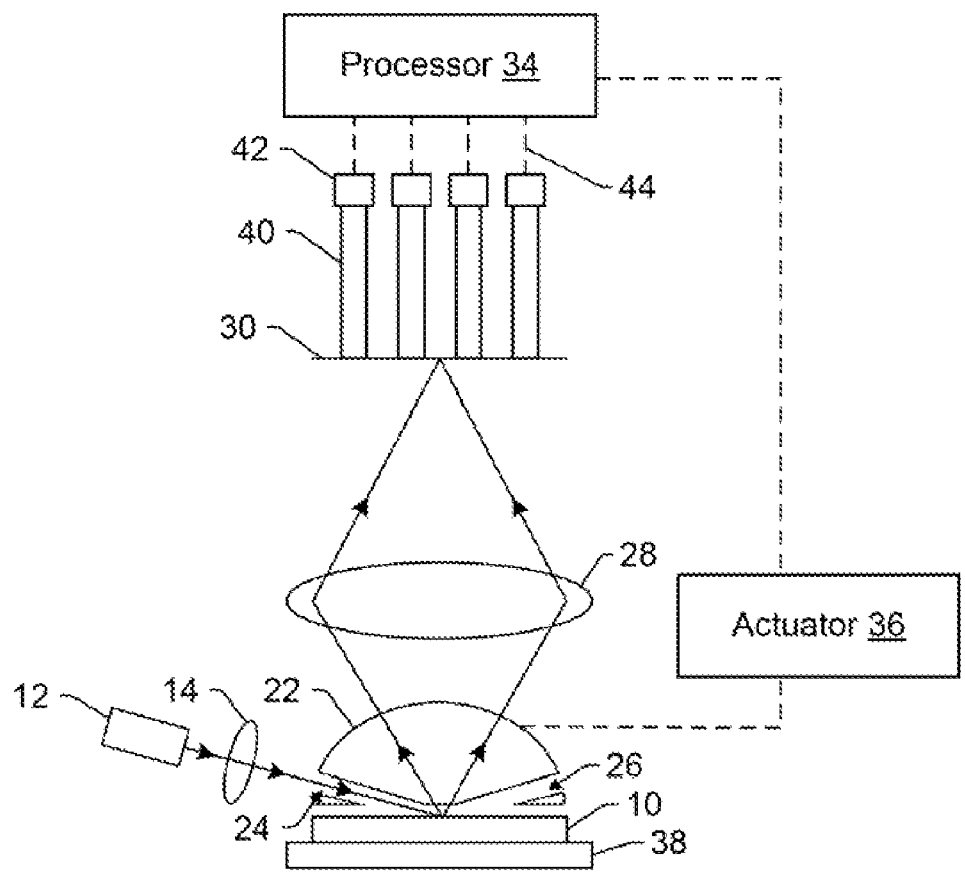
FIGS. 3-5 are schematic diagrams illustrating a cross-sectional view of various embodiments of a system configured to inspect a wafer.

In another embodiment, the detection subsystem includes a set of optical fibers configured to separately transmit the light from the corresponding positions in the image plane to different detectors of the detection subsystem. One embodiment of such a detection subsystem that can be used in the systems described herein is shown in FIG. 3. As shown in FIG. 3, light scattered from different spots within the illuminated area on wafer 10 is collected by the collection subsystem described above and is focused by the collection subsystem to corresponding positions in image plane 30. The number of positions in the image plane to which light is focused will be equal to the number of different spots in the illuminated area from which scattered light is collected (e.g., 8 spots and 8 corresponding positions).

As further shown in FIG. 3, in one embodiment, the detection subsystem includes a set of optical fibers 40. The set of optical fibers is configured to separately transmit the light from the corresponding positions in the image plane to different detectors 42 of the detection subsystem. In other words, individual optical fibers of the set are positioned such that each optical fiber receives light from one corresponding position in the image plane. In this manner, each optical fiber preferably receives light from only one corresponding position in the image plane. Although 4 optical fibers are shown in FIG. 3, the number of optical fibers included in the set is preferably equal to the number of different spots from which light is collected. Furthermore, although the optical fibers are shown in FIG. 3 arranged in a linear array, the optical fibers may be arranged in a two-dimensional array corresponding to the two-dimensional array of the different positions in the image plane.

The diameter of the optical fibers may be selected based on, for example, the size of the different spots on the wafer, the magnification ratio of the collecting and focusing optics, and a selected magnification ratio for the system. The optical fibers may include any suitable optical fibers known in the art that have the selected diameter. Optical fibers having many different diameters are commercially available from various sources known in the art.

As further shown in FIG. 3, in one embodiment, the detection subsystem includes individual detectors 42 that correspond to the different optical fibers. In other words, each of the individual detectors is configured to detect light from one optical fiber. In this manner, each detector preferably detects light from only one position in the image plane. Therefore, although 4 individual detectors are shown in FIG. 3, the number of individual detectors included in the detection subsystem is preferably equal to the number of optical fibers. In this manner, each detector may actually detect the light transmitted by only one optical fiber of the set.

In addition, although the spacing between the optical fibers is shown in FIG. 3 to be relatively constant along the length of the optical fibers, the spacing between the optical fibers may be different at the image plane and at the detectors based on, for example, the separation between the spots on the wafer and the size of the individual detectors. Furthermore, although the individual detectors are shown in FIG. 3 arranged in a linear array, the individual detectors may be arranged in a two-dimensional array corresponding to the two-dimensional array of the different positions in the image plane.

Each detector is configured to generate output responsive to the light detected by the detector. In this manner, the detection subsystem shown in FIG. 3 is configured to generate different output for the light focused to different positions in the image plane. As such, a different signal, different data, etc. can be generated independently for the light scattered from each different spot on the wafer. The signals generated by each detector may be responsive to, for example, an intensity of the light scattered from each of the spots on the wafer. However, the output may be responsive to any measurable property of the light scattered from each of the spots on the wafer. Each of the individual detectors may be, for example, a CCD, a PMT, or any other suitable detector known in the art.

In an alternative embodiment, the detection subsystem may not include the set of optical fibers. In such an embodiment, the individual detectors of the detection subsystem may be arranged such that the photosensitive areas of the detectors are located at the different positions in the image plane. In this manner, the detection subsystem may include multiple detectors as described above or a single detector that can separately detect the light focused to different positions in the image plane.

As shown in FIG. 3, each of the individual detectors may be coupled to processor 34 by transmission medium 44. The transmission media may include any suitable transmission media known in the art. In addition, one or more additional components (not shown) may be interposed between the detectors and the processor such as analog-to-digital converters. Processor 34 may be configured to separately process output from different detectors. For instance, processor 34 may be configured to determine if output from different detectors includes output corresponding to defects. In this manner, the processor may be configured to separately analyze the light scattering from each spot on the wafer. The processor may be further configured as described herein. In addition, the system shown in FIG. 3 may be further configured as described herein.

The embodiments described above, therefore, eliminate several disadvantages of currently used inspection systems. For example, currently used inspection systems include patterned wafer inspection systems. Patterned wafer inspection systems also have issues in terms of the ultimate speed at which they can operate. This issue is effectively addressed by resorting to a multi-spot approach, on an r-θ platform (in which the wafer is rotated and translated simultaneously during inspection). However, if one were to use such an approach and platform at high resolution (e.g., for increased defect detection sensitivity), one would need a mechanism to maintain the focus at all times, which would be impractical for normal, large format, lenses.

The embodiments described herein effectively overcome the sensitivity issues described above and can be used to alter the SP2 systems and other inspection systems in a number of different ways. For example, the ellipsoidal, collector of SP2 systems may be replaced with a miniaturized, well corrected imaging system (e.g., the embodiments of the collection and detection subsystems described above). In addition, the single "wide channel" PMT detector of the SP2 systems may be replaced with a detection subsystem configured as described herein (e.g., including a detector array or an array of optical fibers in the image plane of the imaging system, each of which leads to an individual PMT or avalanche photodiode (APD)) channel).

Using this approach, one achieves a substantial enhancement in signal-to-noise ratio (S/N) compared with the currently used, single large collector, SPx system. In particular, as described above, the haze signal can be reduced by about 2 orders of magnitude, resulting in a factor of about 10 reduction in the shot noise. Secondly, the spatial noise is dramatically reduced as well. In this manner, the capabilities of the SPx family of inspection systems can be extended to the next level of sensitivity. In addition, in certain cases in which the surface roughness of wafers is ordinarily high so that the maximum sensitivity of the SP2 system cannot be achieved, the embodiments described herein may even be capable of achieving that level of sensitivity and performance for such wafers by virtue of such background reductions.

An issue that does arise from such high-resolution imaging applications is the auto-focusing requirements. However, the system embodiments described herein use a miniaturized objective, so that tact focusing can be easily achieved using, for example, piezoelectric actuators. The system embodiments described herein are subject to the same considerations as those pertaining to the SPx systems. Accordingly, if there is a relatively simple auto-focus subsystem that is used in the SPx systems, the same autofocus subsystem could be used in the embodiments of the systems described herein.

Figure 4:
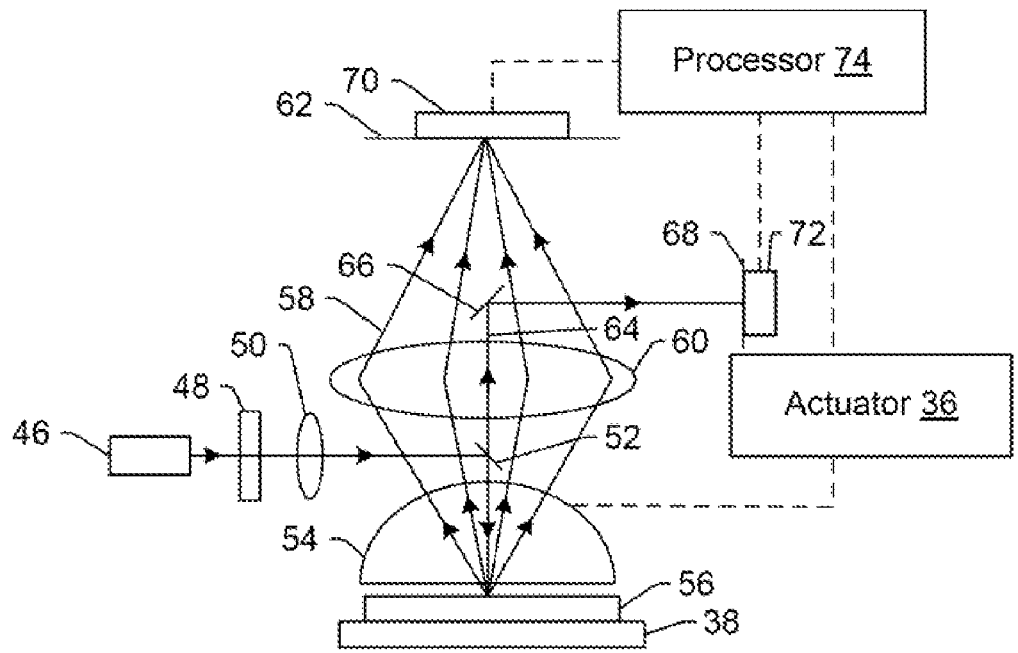

FIG. 4 illustrates another embodiment of a system configured to inspect a wafer. The system shown in FIG. 4 is configured to inspect a patterned wafer although the system may also be used to inspect an unpatterned wafer. The embodiment shown in FIG. 4 uses the general approach described above, which is modified as described further herein such that this approach can be advantageously used for patterned wafer inspection with an r-θ platform (in which the wafer is scanned by rotating and translating the wafer simultaneously). For example, as described further herein, the general approach described above is modified such that for patterned wafer applications, the illumination is normal, rather than oblique, and multi-spot rather than single spot. In particular, the system includes an illumination subsystem configured to simultaneously illuminate multiple spots on the patterned wafer at a substantially normal angle of incidence. The illumination subsystem of the system shown in FIG. 4 includes light source 46, which may include any of die light sources described herein or any other suitable light source known in the art.

The light from the light source is directed to diffractive optical element (DOE) 48 of the illumination subsystem. The DOE may include any suitable DOE. DOE 48 is configured to separate the light from the light source into individual beams. The DOE may also be configured as a high efficiency DOE. In other words, the efficiency of the DOE may be from about 65% to about 75%. The DOE may be further configured to generate individual beams having approximately equal intensity. If the light directed to the DOE is substantially collimated, each of the individual beams generated by the DOE is also substantially collimated.

The DOE may be configured to separate the light into any suitable number of individual beams. In general, a relatively large number of individual beams may be desirable since the number of individual beams determines the number of spots that can be illuminated on the wafer. However, when selecting the number of individual beams, it is important to take into consideration the fact that as the number of individual beams into which the light is separated increases, the complexity of the system also increases. In addition, the DOE may be a diffraction grating that is configured to generate a two-dimensional array of individual beams (instead of a one-dimensional array of individual beams as is usually the case). Diffraction gratings configured to generate a two-dimensional array of individual beams are commercially available from, for example. Heptagon, Espoo, Finland.

If a DOE is used to generate the individual beams that are focused to the wafer, each of the spots illuminated on the wafer may be diffraction limited. In this manner, the illumination subsystem may advantageously have diffraction limited performance. In addition, each of the spots may have a Gaussian profile. In particular, the spots may have Gaussian profiles if the light provided by the light source has a Gaussian profile. In other words, the intensity profiles of the spots illuminated on the wafer may vary depending on the intensity profile of the light directed to the DOE.

The illumination subsystem of the system shown in FIG. 4 also includes refractive optical element 50. Refractive optical element 50 may be configured to focus light exiting DOE 48 to optical element 52. Refractive optical element 50 may be further configured as described herein. Optical element 52 is configured to direct the light from refractive optical element 50 through optical element 54 to wafer 56 at a substantially normal angle of incidence. Optical element 52 may include a reflective or partially reflective optical element. For example, if the system shown in FIG. 4 is configured to inspect the wafer using reflected light, optical element 52 may be configured as a partially transmissive mirror. In another example, if the system shown in FIG. 4 is configured to inspect the wafer without using reflected light, optical element 52 may be configured as a flat or folding mirror.

The multiple spots that are illuminated on the wafer may be configured as described above with respect to the different spots and as shown in FIG. 2 (with the exception that the multiple spots will not be located within a larger illuminated area on the wafer). For example, in one embodiment, the multiple spots do not overlap with each other on the patterned wafer. In another embodiment, a size of each of the multiple spots on the patterned wafer is approximately equal, in an additional embodiment, a size of each of the multiple spots on the patterned wafer is selected such that a substantial amount of the light collected from the multiple spots is not scattered from a surface of the patterned wafer. In a further embodiment, each of the multiple spots is configured such that an amount of haze collected from each of the multiple spots is significantly less than an amount of haze associated with an area covered by all of the multiple spots on the patterned wafer. In some embodiments, each of the multiple spots is configured such that a DC light level due to haze collected from each of the multiple spots is significantly less than a DC light level associated with an area covered by all of the multiple spots on the patterned wafer. In yet another embodiment, each of the multiple spots is configured such that spatial noise collected from each of the multiple spots due to roughness of the patterned wafer is significantly less than spatial noise associated with an area covered by all of the multiple spots on the patterned wafer due to the roughness of the patterned wafer.

The system shown in FIG. 4 also includes a collection subsystem configured to separately collect light from the multiple spots and to focus the light collected from the multiple spots to corresponding positions in an image plane. As described further herein, the collection subsystem (e.g., an objective lens of the collection subsystem) is configured to image scattered and/or reflected light from each of the multiple spots onto a separate channel. The collection subsystem includes optical element 54. Optical element 54 may be configured as described above with respect to optical element 22 shown in FIGS. 1 and 3, with the exception that one or more sections of optical element 54 are not removed as described above. For example, in one embodiment, the collection subsystem includes a miniaturized refractive optical element configured to collect the light from the multiple spots, and in such an embodiment, optical element 54 may be configured as the miniaturized refractive optical element. In another embodiment, the collection subsystem includes a refractive optical element (e.g., optical element 54) configured to collect the light from the multiple spots, and the refractive optical element has a size allowing the system to move the refractive optical element during scanning of the patterned wafer in response to changes in focus of the collection subsystem. The system may be configured to move optical element 54 as described above (e.g., using a control subsystem such as, or including, actuator 36 shown in FIG. 4, which may be configured as described herein). Therefore, the embodiments described herein may use miniaturized optics in a fast focusing set up in conjunction with multi-spot illumination and multi-spot collection. As such, the embodiments described herein can be used to modify the SPx systems to provide ultra-fast, high resolution, patterned wafer inspection.

In one embodiment, the light from the multiple spots that is collected by the collection subsystem includes scattered light. For example, as shown in FIG. 4, optical element 54 may be configured to collect scattered light 58. The collection subsystem may also include refractive optical element 60 that is configured to focus the scattered light collected from the multiple spots to corresponding positions in image plane 62. Refractive optical element 60 may be configured as described above with respect to refractive optical element 28 shown in FIGS. 1 and 3.

In another embodiment, the light from the multiple spots that is collected by the collection subsystem includes reflected light. For example, as shown in FIG. 4, optical element 54 may be configured to collect reflected light 64. The reflected light from the multiple spots may be collected by optical element 54 and directed through optical element 52, which in this embodiment, includes a partially transmissive optical element. Reflected light that passes through optical, element 52 is directed through refractive optical element 60, which directs or focuses the reflected light to reflective optical element 66 of the collection subsystem. Optical element 66 may include any suitable optical element such as a flat or folding mirror. Optical element 66 is configured to direct the reflected light collected from the multiple spots to corresponding positions in image plane 68;

The collection subsystem shown in FIG. 4 may also be configured to separately collect light scattered and reflected from the multiple spots simultaneously. In addition, the collection subsystem shown in FIG. 4 may be configured to focus the reflected and scattered light collected from the multiple spots to corresponding positions in different image planes simultaneously.

The collection subsystem of the system shown in FIG. 4 may be further configured as described herein. For example, in one embodiment, the collection subsystem is corrected such that the light from the multiple spots is imaged to the corresponding positions in the image plane with a defined PSF. Such an embodiment of the collection subsystem may be further configured as described herein.

The system shown in FIG. 4 also includes a detection subsystem configured to separately detect the light focused to the corresponding positions in the image plane and to separately generate output responsive to the light focused to the corresponding positions in the image plane. The output can be used to detect defects one the patterned wafer. In one embodiment, the detection subsystem includes a detector array configured to separately detect the light focused to the corresponding positions in the image plane. For example, if the system is configured to collect light scattered from the multiple spots on the wafer, the detection subsystem may include detector 70, which may include any of the detector arrays described herein. Detector 70 may also be configured as described above with respect to detector 32 shown in FIG. 1. In addition, if the system is configured to collect light reflected from the multiple spots on the wafer, the detection subsystem may include detector 72, which may include any of the detector arrays described herein. Detector 72 may also be configured as described above with respect to detector 32 shown in FIG. 1. Furthermore, detectors 70 and 72 may or may not be the same type of detectors and may or may not have the same configuration.

In different embodiments, the detection subsystem includes a set of optical fibers (not shown in FIG. 4) configured to separately transmit the light from the corresponding positions in the image plane to different detectors (not shown in FIG. 4) of the detection subsystem. For instance, detector 70 and/or detector 72 may be replaced by a set of optical fibers configured to separately transmit the light from the corresponding positions in the image plane to different detectors. A set of optical fibers and different detectors included in the system shown in FIG. 4 in place of detector 70 and/or detector 72 may be configured as described above with respect to FIG. 3.

The output generated by the detection subsystem of the system shown in FIG. 4 may be provided to a processor or computer system. For example, the system shown in FIG. 4 may include processor 74 that is coupled to detectors 70 and 72 (e.g., via one or more transmission media shown by the dashed line between the processor and each of the detectors in FIG. 4, which may include any suitable transmission media known in the art). Processor 74 may be coupled to the detectors such that the processor can receive the output generated by the detectors. The processor may be configured to use the output generated by the detector(s) to detect defects on the wafer. The processor may be configured to detect defects on the wafer using the output generated by the detector(s) as described further herein.

The system shown in FIG. 4 may be configured to scan the light over the wafer in a number of different manners. In addition, since the illumination subsystem of the system shown in FIG. 4 is configured to simultaneously illuminate multiple spots on the wafer at a substantially normal angle of incidence, the manner in which the system scans the light over the wafer may not vary depending on the type of wafer being inspected. For example, in one embodiment, the system is configured to scan light directed to the multiple spots on the wafer across the wafer by simultaneously rotating and translating the wafer. In such embodiments, the wafer may include a patterned wafer or an unpatterned wafer. However, the system may also be configured to scan the light directed to the multiple spots on the wafer across the wafer in the x and y directions. In either embodiment, the system may be configured to scan the light over the wafer by controlling the position of stage 38 as described herein. The system shown in FIG. 4 may be further configured according to any other embodiment(s) described herein.

Figure 5:
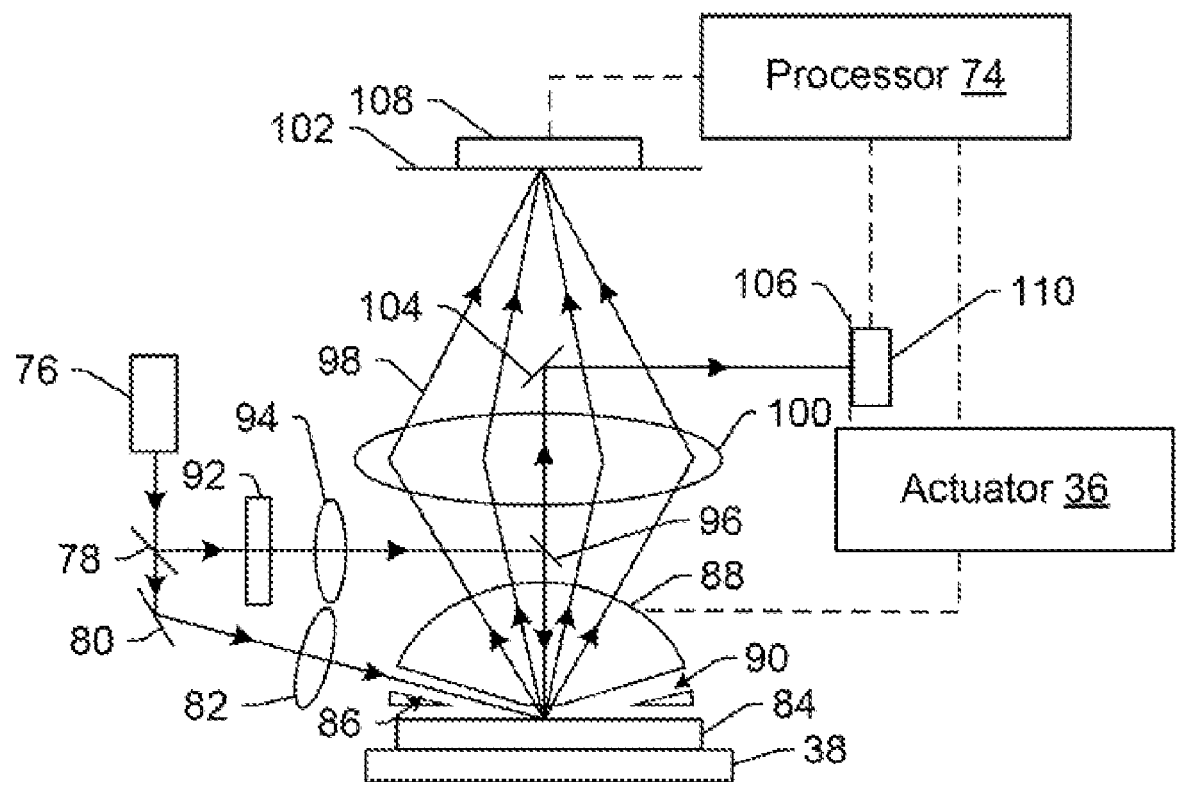

FIG. 5 illustrates another embodiment of a system configured to inspect a wafer. FIG. 5 is essentially a combination of the embodiments shown in FIGS. 1 and 4. For example, in patterned wafer operations, the systems described herein for unpatterned wafer inspection may be used in conjunction with a substantially normal incidence illumination subsystem that produces an array of spots on the wafer. In particular, FIG. 5 includes an illumination subsystem that is configured to direct light to an area on the wafer at an oblique angle of incidence and that, is configured to direct light to multiple spots on the wafer at a substantially normal angle of incidence. In addition, the collection subsystem shown in FIG. 5 is configured to collect light scattered and reflected from the wafer. Furthermore, the system is configured to scan the light over the wafer in the x and y directions and/or to scan the light over the wafer by rotating and translating the wafer simultaneously. Therefore, the system shown in FIG. 5 may be used to inspect a patterned wafer and an unpatterned wafer with oblique single spot illumination and multiple spot collection and detection by scanning the light over the patterned wafer in the x and y directions or by scanning the light, over the unpatterned wafer by rotating and translating the wafer simultaneously (or in the alternative in the x and y directions). In addition, the system shown in FIG. 5 may be used to inspect a patterned wafer and an unpatterned wafer using multi-spot substantially normal incidence illumination and multi-spot collection and detection by scanning light over the patterned or unpatterned wafer in the x and y directions or by rotating and translating the wafer simultaneously.

The system shown in FIG. 5 includes an illumination subsystem configured to illuminate an area on the wafer by directing light to the wafer at an oblique angle of incidence. For example, as shown in FIG. 5, the illumination subsystem includes light source 76, which may include any of the light sources described herein. Light source 76 is configured to direct light to beam splitter 78, which may include any suitable beam splitter known in the art. Beam splitter 78 may be configured to reflect about 50% of the light from the light source and to transmit about 50% of the light. Light transmitted by the beam splitter may be used to illuminate the area on the wafer at an oblique angle of incidence. For example, the light transmitted by beam splitter 78 may be directed to reflective optical element 80, which may include a flat mirror or any other suitable reflective optical element known in the art. Light reflected by reflective optical element 80 is directed to refractive optical element 82, which is configured to focus the light from reflective optical element 80 onto wafer 84. Refractive optical element 82 may be configured as described herein. In addition, refractive optical element 82 may be configured to direct the light to the wafer through section 86 of optical element 88 that is removed. Light directed to the wafer at the oblique angle of incidence that is reflected from the wafer may pass through section 90 of optical element 88 that is also removed. Optical element 88 may be further configured as described herein.

The illumination subsystem is also configured to simultaneously illuminate multiple spots on the wafer at a substantially normal angle of incidence. For example, the illumination subsystem includes DOE 92, refractive optical element 94, and optical element 96. In addition, as shown in FIG. 5, light reflected by beam splitter 78 is directed to DOE 92, which may be configured as described further herein. Light exiting DOE 92 is directed to refractive optical element 94, which focuses the light to optical element 96. Optical element 96 may be further configured as described herein. For example, optical element 96 may be a partially transmissive mirror that reflects the light from refractive optical element 94 and allows light reflected from the wafer to pass therethrough. Optical element 96 is configured to direct the light from refractive optical element 94 through optical element 88 to wafer 84.

The system may also be configured such that light is directed to the water at an oblique angle of incidence or a substantially normal angle of incidence, but not both at the same time. For example, the system may be configured to move one or more optical elements of the illumination subsystem depending on which type of illumination is to be used for inspection (e.g., based on which type of wafer is to be inspected). In one such example, the system may be configured to move reflective optical element 80 into the path of the light transmitted by beam splitter 78 if the oblique angle of incidence illumination will be used for inspection and out of the path of the light transmitted by beam splitter 78 if the substantially normal angle of incidence illumination will be used for inspection. In another such example, the system may be configured to move a shutter (not shown) into the path of the light transmitted by the beam splitter if substantially normal angle of incidence illumination is to be used for inspection or into the path of the light reflected by the beam splitter if oblique angle of incidence illumination is to be used for inspection. The system may be configured to move one or more optical elements of the illumination subsystem in any suitable manner known in the art.

The system shown in FIG. 5 also includes a collection subsystem configured to simultaneously and separately collect light scattered from different spots on the wafer and to focus the light collected from the different spots to corresponding positions in an image plane. For example, the collection subsystem includes optical element 88 configured to simultaneously and separately collect light 98 scattered from different spots on the wafer. Optical element 88 may be configured as described further herein. The collection subsystem may also include refractive optical element 100 configured to focus the light collected from the different spots to corresponding positions in image plane 102. Refractive optical element 100 may be further configured as described herein.

As shown in FIG. 5, light scattered at relatively wide angles (e.g., angles relatively far from normal to the wafer) may be collected and focused to image plane 102. In addition, light scattered at relatively narrow angles (e.g., angles relatively close to normal to the wafer) may be collected and focused to an image plane by the collection subsystem. For example, the collection subsystem may be configured to separately collect light scattered from the different spots (illuminated at an oblique angle of incidence) at relatively narrow angles and to focus the scattered light collected from the different spots to corresponding positions in an image plane. In one such example, the collection subsystem includes optical element 88 that is configured to collect light scattered from the different spots at relatively narrow angles. Scattered light collected by optical element 88 at relatively narrow angles passes through optical element 96 and is focused by refractive optical element 100 to reflective optical element 104, which may be configured as described herein. Reflective optical element 104 directs the light focused by refractive optical element 100 to image plane 106. In another embodiment, oblique incidence illumination scattered at relatively narrow and relatively wide angles may be collected and focused to image plane 102 if optical element 96 and reflective optical element 104 are moved out of the path of the scattered light during inspection.

The collection subsystem is also configured to separately collect light reflected from the different spots (illuminated at a substantially normal angle of incidence) and to focus the reflected light collected from the different spots to corresponding positions in an image plane. For example, the collection subsystem includes optical element 88 that is configured to collect light reflected from the different spots when illuminated at a substantially normal angle of incidence. Reflected light collected by optical element 88 passes through optical element 96 and is focused by refractive optical element 100 to reflective optical element 104, which may be configured as described herein. Reflective optical element 104 directs the light focused by refractive optical element 100 to image plane 106.

The system shown in FIG. 5 also includes a detection subsystem. The detection subsystem is configured to separately detect the light focused to the corresponding positions in the image plane and to separately generate output responsive to the light focused to the corresponding positions in the image plane. The output can be used to detect defects on the wafer. For example, as shown in FIG. 5, the detection subsystem includes detectors 108 and 110. Detector 108 is configured to separately detect the scattered light focused to the corresponding positions in image plane 102 and to separately generate output responsive to the scattered light focused to the corresponding positions in the image plane. Detector 110 is configured to separately detect the reflected or scattered light focused to the corresponding positions in image plane 106 and to separately generate output responsive to the reflected or scattered light focused to the corresponding positions in the image plane. Detectors 108 and 110 and the detection subsystem of the system shown in FIG. 5 may be further configured as described herein.

As shown in FIG. 5, the system includes processor 74, which may be configured as described herein, and actuator 36, which may be configured as described herein. In addition, the system includes stage 38, which may be configured as described herein. In this embodiment, the stage may be configured such that the light can be scanned over the wafer during inspection in the x and y directions. The stage may also be configured such that the light can be scanned over the wafer during inspection by simultaneously rotating and translating the wafer. In this manner, the movement of the stage, and therefore the wafer, during inspection may vary as described above (e.g., based on the type of wafer and the type of illumination used for inspection). The system shown in FIG. 5 may be further configured according to any of the embodiments described herein.

It is noted that FIGS. 1-5 are provided herein to generally illustrate different configurations for the system embodiments described herein. Obviously, the inspection system configurations described herein may be altered to optimize the performance of the inspection system as is normally performed when designing a commercial inspection system. In addition, the systems described herein may be implemented using an existing inspection system (e.g., by modifying an existing inspection system based on the embodiments described herein) such as the SPx series of tools. For some such systems, the operation of the system embodiments described herein may be provided as optional functionality of the system (e.g., in addition to other functionality of the system). In this manner, the embodiments described herein may be used to provide a sensitivity enhancement in detecting relatively small defects in the SPx family of products. Alternatively, the system described herein may be designed "from scratch" to provide a completely new system.

An additional embodiment relates to a method for inspecting a wafer. The method includes illuminating an area on the wafer by directing light to the wafer at an oblique angle of incidence. The method also includes simultaneously collecting light scattered from different spots within the illuminated area and focusing the light collected from the different spots to corresponding positions in an image plane. The different spots may be configured according to any of the embodiments described herein. In addition, the method further includes separately detecting the light focused to the corresponding positions in the image plane and separately generating output responsive to the light focused to the corresponding positions in the image plane. The method further includes detecting defects on the wafer using the output.

In one embodiment, the wafer includes a patterned wafer, and the method includes scanning the light directed to the patterned wafer across the patterned wafer in x and y directions. In a different embodiment, the method includes scanning the light directed to the wafer across the wafer by simultaneously rotating and translating the wafer.

In one embodiment, illuminating the area cm the wafer includes directing the light through a removed section of an optical element, which collects the light scattered from the different spots, to the area on the wafer at the oblique angle of incidence. In another embodiment, the method includes moving a refractive optical element, which collects the light scattered from the different spots, during scanning of the light over the wafer in response to changes in focus of a collection subsystem. In an additional embodiment, focusing the light collected from the different spots to corresponding positions in an image plane includes imaging the light scattered from the different spots to the corresponding positions in the image plane with a defined PSF. In a further embodiment, the method includes separately transmitting the light from the corresponding positions in the image plane to different detectors, which separately detect the light focused to the corresponding positions in the image plane.

Each of the steps of each of the embodiments of the method described above may be performed as described further herein. Each of the embodiments of the method described above may include any other step(s) described herein. In addition, each of the embodiments of the method described above may be performed by any of the system embodiments shown in FIGS. 1, 3, and 5.

A further embodiment relates to another method for inspecting a patterned wafer. This method includes simultaneously illuminating multiple spots on the patterned wafer at a substantially normal angle of incidence. The multiple spots may be configured according to any of the embodiments described herein. The method also includes separately collecting light from the multiple spots and focusing the light collected from the multiple spots to corresponding positions in an image plane. In addition, the method includes separately detecting the light focused to the corresponding positions in the image plane and separately generating output responsive to the light focused to the corresponding positions in the image plane. The method further includes detecting defects on the patterned wafer using the output.

In one embodiment, the light from the multiple spots includes scattered light. In another embodiment, the light from the multiple spots includes reflected light.

In one embodiment, the method includes moving a refractive optical element, which collects the light from the multiple spots, during scanning of the patterned wafer in response to changes in focus of a collection subsystem that includes the refractive optical element. In another embodiment, focusing the light collected from the multiple spots to corresponding positions in an image plane includes imaging the light from the multiple spots to the corresponding positions in the Image plane with a defined PSF. In an additional embodiment, the method includes scanning light directed to the multiple spots on the patterned wafer across the patterned wafer by simultaneously rotating and translating the patterned wafer. In a further embodiment, the method includes separately transmitting the light from the corresponding positions in the image plane to different detectors, which separately detect the light focused to the corresponding positions in the image plane.

Each of the steps of each of the embodiments described above may be performed as described further herein. Each of the embodiments of the method described above may include any other step(s) described herein. In addition, each of the embodiments of the method described above may be performed by any of the system embodiments shown in FIGS. 4 and 5.

In some embodiments, the systems described herein may be configured as a "stand alone tool" or a tool that is not physically coupled to a process tool. However, such a system may be coupled to the process tool by a transmission medium, which may include wired and wireless portions. The process tool may include any process tool known in the art such as a lithography tool, an etch tool, a deposition tool, a polishing tool, a plating tool, a cleaning tool, or an ion implantation tool. The process tool may be configured as a "cluster tool," or a number of process modules coupled by a common handler.

The results of inspection performed by the embodiments described herein may be used to alter a parameter of a process or a process tool using a feedback control technique, a feed-forward control technique, or an in situ control technique. The parameter of the process or the process tool may be altered manually or automatically.

Further modifications and alternative embodiments of various aspects of the invention may be apparent to those skilled in the art in view of this description. For example, systems configured to inspect a wafer are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to inspect a wafer, comprising:
   an illumination subsystem configured to illuminate an area on the wafer by directing light to the wafer at an oblique angle of incidence;
   a collection subsystem configured to simultaneously collect light scattered from different spots within the illuminated area and to focus the light collected from the different spots to corresponding positions in an image plane, wherein the different spots are spatially separated from each other within the illuminated area on the wafer, and wherein each of the different spots is configured such that an amount of haze collected from each of the different spots is significantly less than an amount of haze associated with the illuminated area on the wafer; and
   a detection subsystem configured to separately detect the light focused to the corresponding positions in the image plane and to separately generate output responsive to the light focused to the corresponding positions in the image plane, wherein the output can be used to detect defects on the wafer.

2. The system of claim 1, wherein the different spots within the illuminated area do not overlap with each other within the illuminated area.

3. The system of claim 1, wherein a size of each of the different spots on the wafer is approximately equal.

4. The system of claim 1, wherein each of the different spots is further configured such that a direct current light level due to the haze collected from each of the different spots is significantly less than a direct current light level due to the haze associated with the illuminated area on the wafer.

5. The system of claim 1, wherein each of the different spots is further configured such that spatial noise collected from each of the different spots due to roughness of the wafer is significantly less than spatial noise associated with the illuminated area on the wafer due to the roughness of the wafer.

6. The system of claim 1, wherein the collection subsystem comprises an optical element configured to simultaneously collect the light scattered from the different spots, and wherein a section of the optical element is removed such that the illumination subsystem can direct the light through the section to the area on the wafer at the oblique angle of incidence.

7. The system of claim 1, wherein the wafer comprises an unpatterned wafer.

8. The system of claim 1, wherein the wafer comprises a patterned wafer, and wherein the system is further configured to scan the light directed to the patterned wafer across the patterned wafer in x and y directions.

9. The system of claim 1, wherein the collection subsystem comprises a miniaturized refractive optical element configured to simultaneously collect the light scattered from the different spots.

10. The system of claim 1, wherein the collection subsystem comprises a refractive optical element configured to simultaneously collect the light scattered from the different spots, and wherein the refractive optical element has a size allowing the system to move the refractive optical element during scanning of the light over the wafer in response to changes in focus of the collection subsystem.

11. The system of claim 1, wherein the collection subsystem is corrected such that the light scattered from the different spots is imaged to the corresponding positions in the image plane with a defined point spread function.

12. The system of claim 1, wherein the system is further configured to scan the light directed to the wafer across the wafer by simultaneously rotating and translating the wafer.

13. The system of claim 1, wherein the detection subsystem comprises a detector array configured to separately detect the light focused to the corresponding positions in the image plane.

14. The system of claim 1, wherein the detection subsystem comprises a set of optical fibers configured to separately transmit the light from the corresponding positions in the image plane to different detectors of the detection subsystem.

15. A system configured to inspect a patterned wafer, comprising:
an illumination subsystem configured to simultaneously illuminate multiple spots on the patterned wafer at a substantially normal angle of incidence;
a collection subsystem configured to separately collect light from the multiple spots and to focus the light collected from the multiple spots to corresponding positions in an image plane, wherein each of the multiple spots is configured such that an amount of haze collected from each of the multiple spots is significantly less than an amount of haze associated with an area covered by all of the multiple spots on the patterned wafer; and
a detection subsystem configured to separately detect the light focused to the corresponding positions in the image plane and to separately generate output responsive to the light focused to the corresponding positions in the image plane, wherein the output can be used to detect defects on the patterned wafer.

16. The system of claim 15, wherein the multiple spots do not overlap with each other on the patterned wafer.

17. The system of claim 15, wherein the light from the multiple spots comprises scattered light.

18. The system of claim 15, wherein the light from the multiple spots comprises reflected light.

19. The system of claim 15, wherein a size of each of the multiple spots on the patterned wafer is approximately equal.

20. The system of claim 15, wherein each of the multiple spots is further configured such that a direct current light level due to the haze collected from each of the multiple spots is significantly less than a direct current light level due to the haze associated with the area covered by all of the multiple spots on the patterned wafer.

21. The system of claim 15, wherein each of the multiple spots is further configured such that spatial noise collected from each of the multiple spots due to roughness of the patterned wafer is significantly less than spatial noise associated with the area covered by all of the multiple spots on the patterned wafer due to the roughness of the patterned wafer.

22. The system of claim 15, wherein the collection subsystem comprises a miniaturized refractive optical element configured to collect the light from the multiple spots.

23. The system of claim 15, wherein the collection subsystem comprises a refractive optical element configured to collect the light from the multiple spots, and wherein the refractive optical element has a size allowing the system to move the refractive optical element during scanning of the patterned wafer in response to changes in focus of the collection subsystem.

24. The system of claim 15, wherein the collection subsystem is corrected such that the light from the multiple spots is imaged to the corresponding positions in the image plane with a defined point spread function.

25. The system of claim 15, wherein the system is further configured to scan light directed to the multiple spots on the patterned wafer across the patterned wafer by simultaneously rotating and translating the patterned wafer.

26. The system of claim 15, wherein the detection subsystem comprises a detector array configured to separately detect the light focused to the corresponding positions in the image plane.

27. The system of claim 15, wherein the detection subsystem comprises a set of optical fibers configured to separately transmit the light from the corresponding positions in the image plane to different detectors of the detection subsystem.

28. The system of claim 1, wherein a size of each of the different spots on the wafer is selected such that a substantial amount of the light scattered from the different spots is not scattered from a surface of the wafer.

29. The system of claim 15, wherein a size of each of the different spots on the wafer is selected such that a substantial amount of the light scattered from the different spots is not scattered from a surface of the wafer.

* * * * *